(12) United States Patent
Kiluk

(10) Patent No.: US 10,512,530 B2
(45) Date of Patent: Dec. 24, 2019

(54) ELECTRIC TOOTHBRUSH

(76) Inventor: Sebastian Kiluk, Zakliczyn (PL)

(*) Notice: Subject to any disclaimer, the term of this patent is extended or adjusted under 35 U.S.C. 154(b) by 700 days.

(21) Appl. No.: 14/345,715

(22) PCT Filed: Sep. 13, 2012

(86) PCT No.: PCT/EP2012/067940
§ 371 (c)(1),
(2), (4) Date: Mar. 19, 2014

(87) PCT Pub. No.: WO2013/041438
PCT Pub. Date: Mar. 28, 2013

(65) Prior Publication Data
US 2014/0215732 A1    Aug. 7, 2014

(30) Foreign Application Priority Data
Sep. 19, 2011   (PL) ..................... P-396377

(51) Int. Cl.
*A61C 17/26*    (2006.01)
*A61C 17/22*    (2006.01)

(52) U.S. Cl.
CPC .......... *A61C 17/26* (2013.01); *A61C 17/221* (2013.01)

(58) Field of Classification Search
CPC ....... A61C 17/26; A61C 17/221; A61C 17/34; A61C 17/225; A46B 9/04; A47L 11/4038; A47L 11/164; B24D 13/147; B24D 13/20; B24D 9/08
USPC ............................. 14/143.1, 22.1, 167.1, 116
See application file for complete search history.

(56) References Cited

U.S. PATENT DOCUMENTS

| | | | | |
|---|---|---|---|---|
| 2,279,982 A * | 4/1942 | Glynn | ................ | A61C 17/26 15/23 |
| 4,603,448 A * | 8/1986 | Middleton | ............ | A61C 17/26 15/22.1 |
| 5,794,296 A * | 8/1998 | Wong | ................ | A61C 17/26 15/22.1 |

FOREIGN PATENT DOCUMENTS

DE      20321083 U1    11/2005

* cited by examiner

Primary Examiner — Robert J Scruggs
(74) Attorney, Agent, or Firm — Jacob Eisenberg

(57) ABSTRACT

An electric toothbrush including a handle, a head movable with respect to said handle, and a rotating working element having at least one brush located out of the geometric axis of said handle. The electric toothbrush further includes an electric motor for driving the working element in a rotary movement in a clockwise/counterclockwise direction, and a motor rotation direction switch coupled functionally with the head and the handle. The head and the handle are coupled with resilient technical means that enable, after exertion of the torque to the head, to rotate the head with respect to the handle into the left or right positions, where the motor rotation direction switch turns on the motor in the clockwise/counterclockwise rotation direction. After releasing said torque, the resilient technical means enable to maintain the head in a standby position relative to the handle, where the motor rotation direction switch turns off the motor.

10 Claims, 8 Drawing Sheets

ELECTRIC TOOTHBRUSH

This application is a national phase application under 35 U.S.C. § 371 of International Application Serial No. PCT/EP2012/067940 filed on Sep. 13, 2012, and claims the priority under 35 U.S.C. § 119 to Polish Patent Application No. P-396377, filed on Sep. 19, 2011, which are hereby expressly incorporated by reference in their entirety for all purposes.

TECHNICAL FIELD

The subject of the present invention is an electric toothbrush having a head part with a rotating working element and equipped with technical means to drive said working element and to change the direction of its rotating movement.

BACKGROUND OF THE DISCLOSURE

Electric toothbrushes having a head with a rotating working element in the form of a single cylindrical brush or in the form of a pair of brushes are becoming an increasingly common hygiene tool allowing effective removal of deposits from teeth.

For proper and effective teeth cleaning, including spaces in between teeth, it is necessary to apply the movement of the toothbrush head in a direction such that the bristles move in a rotating manner from the gums towards the biting edge of the teeth.

During the cleaning of the front and rear tooth surfaces and of the upper and lower jaw teeth, the rotating movement of the brush has to be reversed; thus, known toothbrushes are equipped with technical means that enable said change of the rotation direction.

Known toothbrushes of such kind typically contain a handle with extending head, said head having at its end a rotating cylindrical brush or a pair of brushes rotating in opposite directions.

Known toothbrushes typically contain driving motors, electric power sources, and electric equipment inside the handle, said equipment allowing at least to switch the motor on and off. The neck part of said toothbrushes contains an element linking the motor with the rotating brush head.

A number of such devices have been presented in patent literatures. As an example, an electric toothbrush known from the description of the U.S. Patent Application Publication No. 2008052845 is equipped with two brushes with parallel rotation axes, allowing to simultaneously brush both sides of the teeth in a direction form the gum line toward the teeth crowns. To reduce a possible injury of the inner cheek said brushes are partially covered with a casing. The toothbrush is additionally equipped with a manual switch to turn on and change the rotation direction of said brushes.

Another electric toothbrush, described in U.S. Pat. No. 4,163,300, includes an elongated body member having a cylindrical brush mounted coaxially therewith at one end thereof. The brush is driven in a rotatable way by a reversible electric motor located in the handle and having an automatic reversing weight-driven switch responsive to the position in which the handle is held to cause rotation of the brush such that its bristles move in a direction from the gum line towards the crowns of the teeth.

A toothbrush with a gravitation-driven switch of the direction of rotation of the brush, is known from the description of the U.S. Pat. No. 4,709,438, said toothbrush having a headpiece with a cylindrical brush and a handle. The cylindrical brush is located coaxially with respect to the handle. By means of a gravity switch, the direction of the rotation of the brush is reversed according to the turning movement of the handle in order to automatically maintain a direction of the rotation of the brush from the gums to the crown of the teeth. In order to obtain the correct position of the toothbrush, the brush is provided with a protecting cap leaving an opening allowing to form a working zone. The gravity switch is arranged parallel to the plane of the working zone of the brush.

From the description of the German utility model NO. DE 20321083U, an electric toothbrush is known containing a handle and a headpiece with a cylindrical brush rotating in two opposite directions. The rotation direction of the brush can be changed with a manual switch. The rotating brush is coupled with an electric motor by the shaft and toothed gear or belt transmission. The headpiece is located eccentrically to the longitudinal axis of the handle and a shield attached to the head surrounds more than a half of the brush ambit. As a result, when used, the brush is placed horizontally such that the direction of its movement is consistent with the orientation of the teeth and the gaps between the teeth.

An automatic toothbrush as claimed in the European Patent Application NO. EP 0240469 has a cylindrical paint-brush-like rotor able to rotate in opposite directions selected by an automatic control unit. The brush is located coaxially to the longitudinal axis of the handle. The change of the brush rotation direction is obtained with two opposite longitudinal edges of a shell which partially covers the swab-like rotor and is rotatably mounted to the handle. When one edge of the shell gets in contact with the gums or the tooth, the shell forced by the pressure rotates with respect to the handle, moving the contacts of the rotation direction switch.

In the U.S. Pat. No. 5,794,296, an electric toothbrush is disclosed having a rotary brush located coaxially to the longitudinal axis of the handle. The direction of the rotation of the brush is automatically controlled depending on whether the top or the bottom teeth are being brushed, in order to brush any food debris present on the teeth and gums in a direction away from the gums. The toothbrush according to this invention utilizes a direction controller that is placed inside the mouth between the top and bottom teeth. The direction controller switches the direction of brush rotation and serves to stabilize the toothbrush relative to the teeth during the brushing operation. The rotation of the direction controller with respect to the handle, operates a reversing switch to change the direction of rotation of the brush, as required to brush in a direction away from the gums and towards the teeth, without removing the toothbrush from the mouth. The direction controller is a narrow frame-shaped element oriented along the generating line of the cylindrical brush and attached rotatably with respect to the handle.

From the description of U.S. Pat. No. 3,829,922, an electric toothbrush is provided with a handle and coaxially located rotary brush, said brush being driven by a reversible electric motor placed inside the handle. The rotation direction of the electric motor is controlled by a reversing switch. For this purpose the toothbrush is equipped with a longitudinally extending shield located at the end of the control lever of the switch. Close to the opposite end, the lever is supported in the handle such that the pendulous movement of the lever with respect to the handle is possible in a plane substantially parallel to the axis of the brush rotation, from first active position—when the end of the shield is placed on one side of the brush and the brush is rotating in the first direction, through the neutral position—when the drive is switched off—until the second active position—when the end of the shield is placed on another side of the brush and the brush is rotating in the opposite direction. Movement of the shield away from the normal position, perpendicular to the rotation axis of the brush rotation in one or the other active position is transferred to the coupled end of the lever to the reversing switch to change the direction of the rotation of the motor and thereby the rotary brush. The return movement of the lever with attached shield to the neutral position, wherein the motor is switched off, is forced by the spring attached inside the handle and coupled to the lever.

From the description of French Patent No. FR 2891452, an electric toothbrush is provided with a cylindrical headpiece rotating in directions changed by the pressure force of the tooth directed obliquely with respect to the longitudinal axis of the handle. The toothbrush is equipped with a cylindrical brush designed to rotate away from the gums and towards the teeth. The brush, which is removable from the handle, is connected to gears with a shaft inside a casing, which forms the neckpiece of the toothbrush. Forced by the pressure of the headpiece on the teeth, the casing flips from one position to the other, causing its other end, projecting into the handle, to switch the contacts controlling the direction of the electric motor rotation. The casing is supported in a handle by a median pivot, allowing for the movement in a plane substantially parallel to the longitudinal axis of the handle, similarly to the guard lever of the headpiece known from the description of U.S. Pat. No. 3,829,922.

The rotating cylindrical brush is located at the end of the casing obliquely with respect to the longitudinal axis of the handle to enforce on the user proper placement during brushing. Particularly, the direction of the brush rotation is aligned with the orientation of the teeth and the gaps between the teeth, and simultaneously enables the inclination of the casing with respect to the handle, caused by the pressure force of the headpiece on the teeth, and to move the casing into position wherein the end of the casing placed inside the handle switches the contacts controlling the motor rotation direction, such that the brush rotates from the gums to the crown of the teeth.

SUMMARY OF THE INVENTION

The technical problem to be resolved is to obtain an electric toothbrush with a construction in which the rotation direction of the working element is changed automatically, said change being caused by the change of the orientation and direction of the force pressing the working element towards the teeth, such that when brushing the teeth, the working element always rotates in the direction from the gums to the biting edge of the teeth.

This technical problem has been solved with a rotating arrangement of the head of the toothbrush in the handle, said head of the toothbrush comprising a rotating working element, and by the eccentric location of the rotating working element of the head of the toothbrush with respect to the rotation axis of the head with respect to the base, while coupling the electric contacts of the rotation direction switch of the motor driving the working element with the head and the handle of the toothbrush and activating said switch by relative rotation of the head and the handle.

According to the invention, the electric toothbrush comprises a handle and a head movable with respect to said handle and provided with a rotating working element having at least one brush, said working element located out of the geometric axis of said handle. The electric toothbrush has in addition an electric motor for driving the working element in a rotary movement in a clockwise or counterclockwise direction and has a motor rotation direction switch, coupled functionally with the head and the handle. The head is joined with the handle by a rotating coupling, and the working element is mounted in the head and located out of the rotation axis of the head with respect to the handle, wherein the head and the handle are coupled with resilient technical means.

The toothbrush is characterized in that said technical means enable, after exertion of the torque to the head, to rotate the head with respect to the handle into the left or the right position, where the motor rotation direction switch turns on the motor in the clockwise or counterclockwise rotation direction and after release of said torque, said resilient technical means enable to maintain the head in a standby position relative to the handle, where the motor rotation direction switch coupled with the head and the handle turns off the motor.

In particular, it is preferred when the head of the toothbrush is pivotally mounted in the handle trough the base of the head and when the base is coupled with the resilient element of the handle, especially such as a radially situated rib, or when the base of the head includes a resilient protrusion coupled with the elements, particularly such as a pair of inner ribs positioning the protrusion with respect to the handle.

According to the invention, the working element which is mounted in the head of the toothbrush is a cylindrically shaped brush with the rotation axis shifted eccentrically with respect to the rotation axis of the head base with respect to the handle. Alternatively, a pair of cylindrically shaped brushes in the fixtures located eccentrically with respect to the rotation axis of the base of the head with respect to the handle, is mounted in the head of the toothbrush. In one preferred embodiment of the invention, said pair of brushes is located next to each other, at such an angle that their rotation axes intersect outside the contour of the handle. In another preferred embodiment of the invention, said pair of brushes is located next to each other, at such an angle that their rotation axes intersect at an obtuse angle, but not outside the contour of the handle, preferably at such an angle that their rotation axes are parallel and do not intersect at all.

In the enhanced embodiment of the invention, when the base of the head is coupled with the resilient part of the handle, such as a radially situated rib, it is preferred that the base has a longitudinal axial slit with edges placed at a distance from both sides of the base of the rib, which is located in the handle, said rib being fitted (shape coupled) into the base of the head. Then, to obtain switching of the motor rotation direction, it is best to provide the rib with the first electric contact of the switch for the control of the motor rotation direction, and to provide the edges of said slit with another two electric contacts, each placed at a distance on both sides of the first contact.

In another enhanced embodiment of the invention, when the base of the head is provided with a resilient protrusion coupled with the elements positioning the protrusion with respect to the handle, particularly such as a pair of ribs, it is preferred that the base of the head is equipped with the second stiff protrusion, preferably placed against the first resilient protrusion. Then, to construct the switch of the motor rotation direction it is preferred to provide the second protrusion on the base of the head with one electric contact, and to attach two electric contacts of the switch for changing the motor rotation direction, each placed on the handle at a distance on both sides of the first contact. Alternatively, to construct the switch of the motor rotation direction, it is also possible that the second protrusion of the base of the head is provided with a pair of the first electric contacts of the switch for changing the motor rotation direction, and two pairs of the second electric contacts are attached to the handle, said pairs of the second electric contacts being placed at a distance on both sides of the first pair of the contacts.

The invention fully resolves the technical problem. The construction of the toothbrush enforces the user to position the toothbrush in such manner that during the brushing action, the rotating working element of the head is directed towards the gum and the head is essentially placed in line with the biting edge of the teeth. According to the invention, the space between the gum or the tooth and the cheek allows only for the placement of the head brush or brushes in a position wherein the pressure of the brush on the tooth produces a torque that causes a rotational movement of the head with the brush with respect to the handle, due to the eccentric placement of the working element with respect to the axis of the rotation of the head in the handle.

Starting the motor and changing the motor direction rotation require the user to place the working element of the toothbrush against the tooth and firmly press the working element against the tooth, or require the user to place the working element against the tooth and rotate the handle in the direction form the gums to the biting edge of the teeth. However, the release of the pressure of the working element on the tooth, or the rotation of the handle opposite to said direction turns off the motor driving the brush, because the head and the handle move to the standby (equilibrium) position under the effect of said resilient technical means joining the head and the handle.

BRIEF DESCRIPTION OF THE DRAWINGS

Three preferred embodiments of the invention are shown in the attached drawing, in which.

DETAILED DESCRIPTION OF THE INVENTION

In all three embodiments, the toothbrush is equipped with a handle 1 having a cylindrical plastic body. However, it is understandable that in other embodiments, the handle can have the form other than cylindrical.

Figure 1:
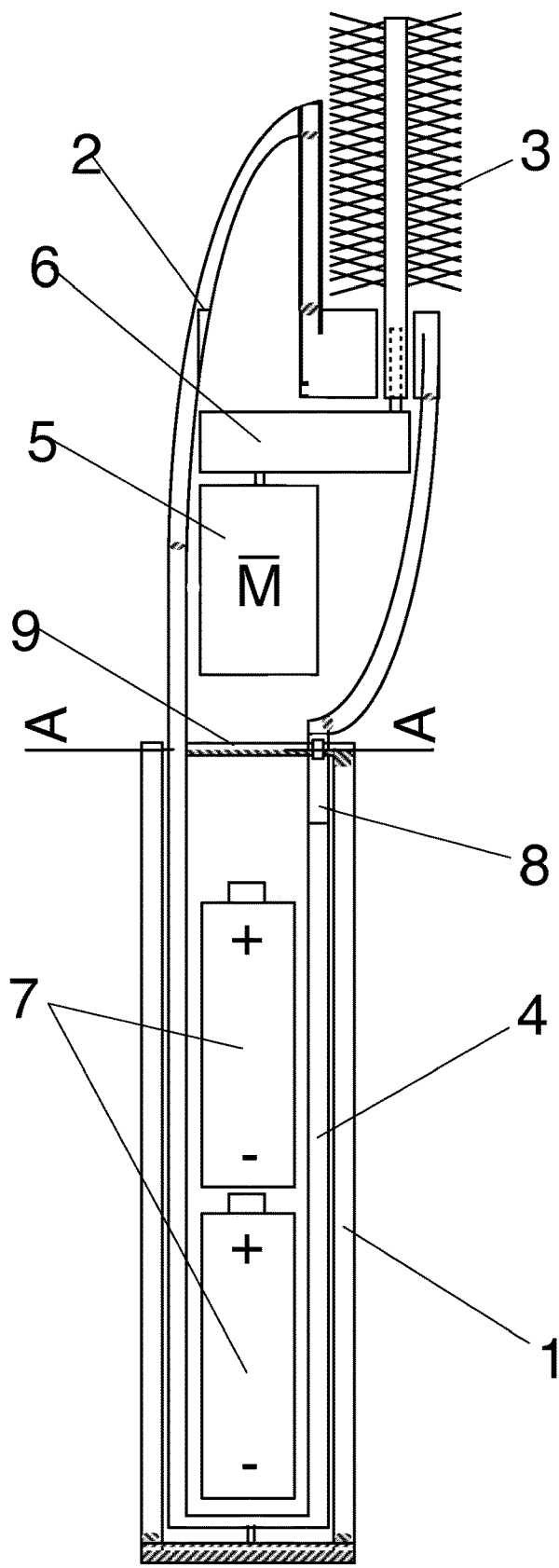
FIG. 1 illustrates a longitudinal section of the toothbrush according to the first embodiment.
Figure 4:
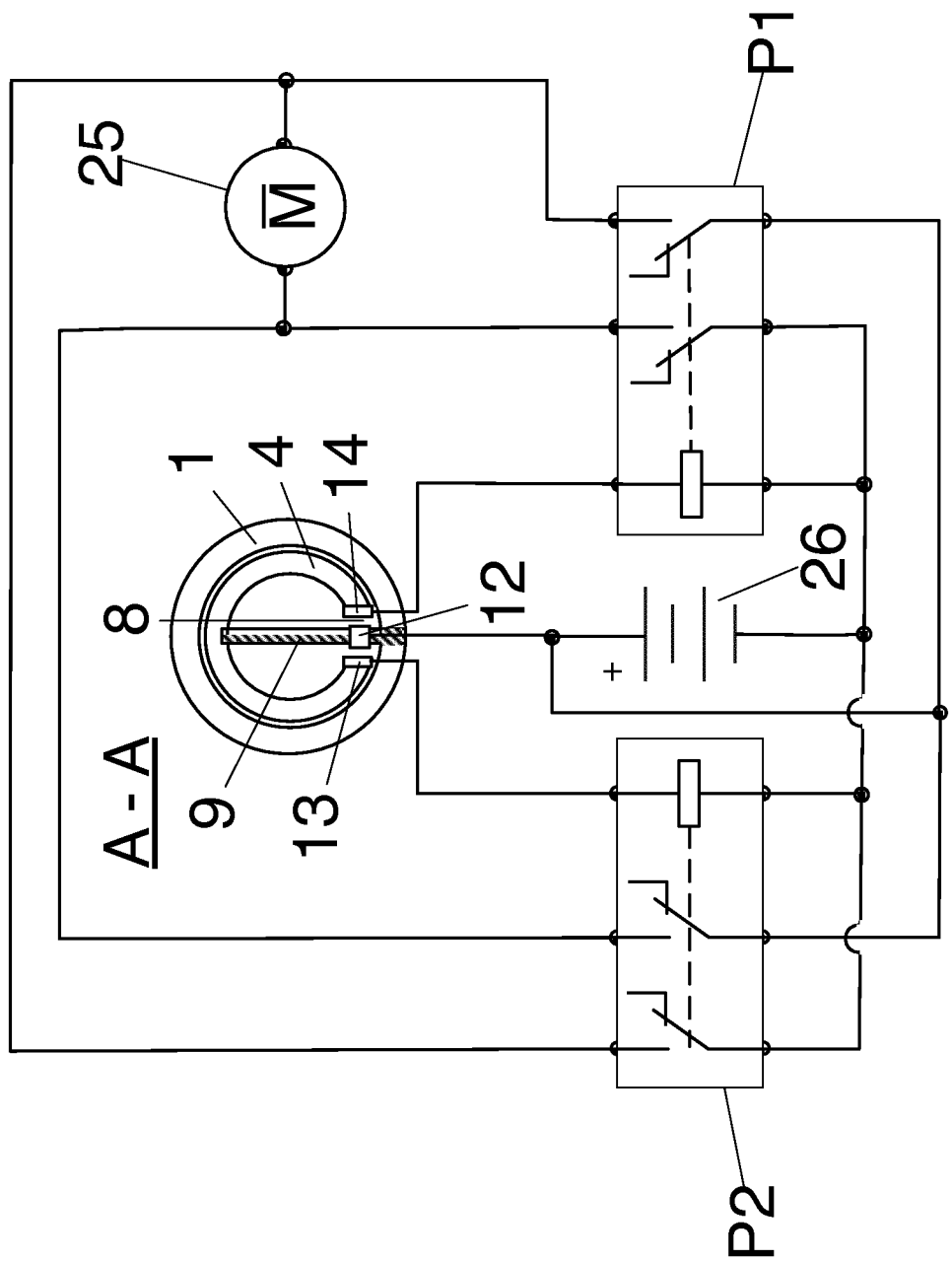
FIG. 4 is a cross-section along the line A-A of FIG. 1 with an example of the wiring diagram of the toothbrush.

In the first example, shown in FIGS. 1 and 4, the toothbrush has a head part 2, which is empty inside and has a single cylindrical brush 3 constituting the working element of the toothbrush. The brush 3 can rotate in two directions, i.e., to the right (clockwise) or to the left (counterclockwise).

In the first embodiment, the head 2 is located directly next to the handle 1 and pivotally mounted in the handle by means of a cylindrical base 4, which extends inside along basically the entire handle 1.

The brush 3 is driven by an electric motor 5 with the transmission 6 fitted inside the head 2 and coupled with the brush 3. The power source 7 of the motor 5, in the form of galvanic cells or accumulators, is located in the cylindrical base 4 of the head 2.

The cylindrical base 4 of the head 2 has a rotating coupling means in the form of a longitudinal slit 8 which is placed axially at one end, while the body of the handle 1 contains a resilient joint or a resilient technical means in the form of a rib 9, said rib 9 being placed at the other end of said handle 1 near the head part 2. The rib 9 is situated radially and its end cooperates in shape with the casing of the cylindrical base 4 of the head 2. Thus, the cylindrical base 4 of the head 2 can rotate with respect to the handle 1 by a small acute angle in both directions, i.e., to the right and to the left from the standby (equilibrium) position, in which it is kept by the resilient rib 9 of the handle 1. It is therefore obvious that in order to make said movement possible, the width of the slit 8 in the base 4 of the head 2 should be larger than the width of the rib 9.

At the end opposite to the handle 1, the head 2 of the toothbrush contains a recess, wherein the brush 3 is pivotally mounted through a bearing, and the axis of the rotation of the brush 3 is placed eccentrically with respect to the axis of the rotation of the base 4 of the head 2 with respect to the handle 1. Owing to the eccentric arrangement of said elements, when the user presses the bristle of the brush 3 against the teeth 10, the pressure force of the teeth 10 on said brush 3 causes the rotation of the head 2 with respect to the handle 1 from the standby (equilibrium) position to the right or to the left, depending on the orientation and direction of the pressure force of the teeth 10 on said brush 3.

To exploit the relative rotational movement of the head 2 and the handle 1 to start and stop the motor 5 and to change the motor 5 rotation direction to the right or to the left in such a manner that the brush 3 always rotates in the direction from the gums 11 to the biting edge of the teeth 10, a resilient rib 9 is equipped at its base with the first electric contact 12, fixed (i.e. maintaining a constant position) against the handle 1, and the edges of a longitudinal slit 8 in the cylindrical casing of the base 4 of the head 2 adjacent to the rib 9, are equipped with the second 13 and third 14 electric contacts movable with respect to the handle 1, said contacts (second contact 13 and third contact 14) being able to contact with the first contact 12 when the head 2 is turned to the right or to the left from the standby (equilibrium) position, whereby when all contacts 12, 13, 14 are connected with the wires of the control circuit, the motor 5 may be started to rotate to the right or to the left. It is entirely understandable that when the head 2 is in the standby (equilibrium) position, in which it is kept by the resilient rib 9, said contacts 12, 13, 14 are set apart from each other, and the motor is turned off. Similarly, for experts it is understandable that said contacts 12, 13, 14 should be connected to the motor 5 and the power source 8 with the wires of the electric circuit as shown for example in FIG. 4.

It is thus understandable that for better readability of the drawing, the electric wiring of the toothbrush was omitted in FIG. 1, but to enable an expert to carry out the invention, FIG. 4 shows an example of the scheme of the mechanical-electrical system for powering on, powering off, and changing the direction of the motor 5 rotation, said motor 5 containing two relays, P1 and P2.

Figure 2:
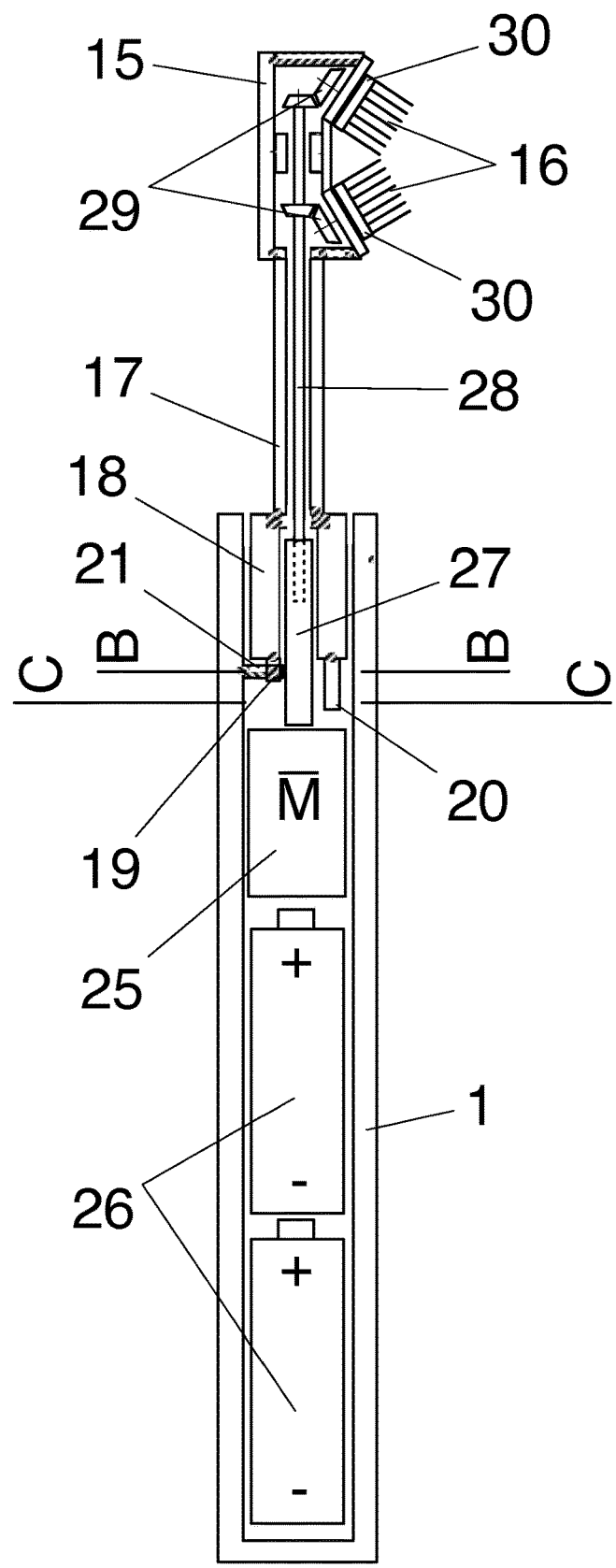
FIG. 2 illustrates a longitudinal section of the toothbrush in the second embodiment.
Figure 3:
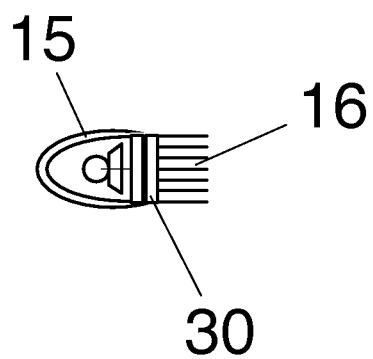
FIG. 3 is a view from the front of the head of the toothbrush shown in FIG. 2.
Figure 5:
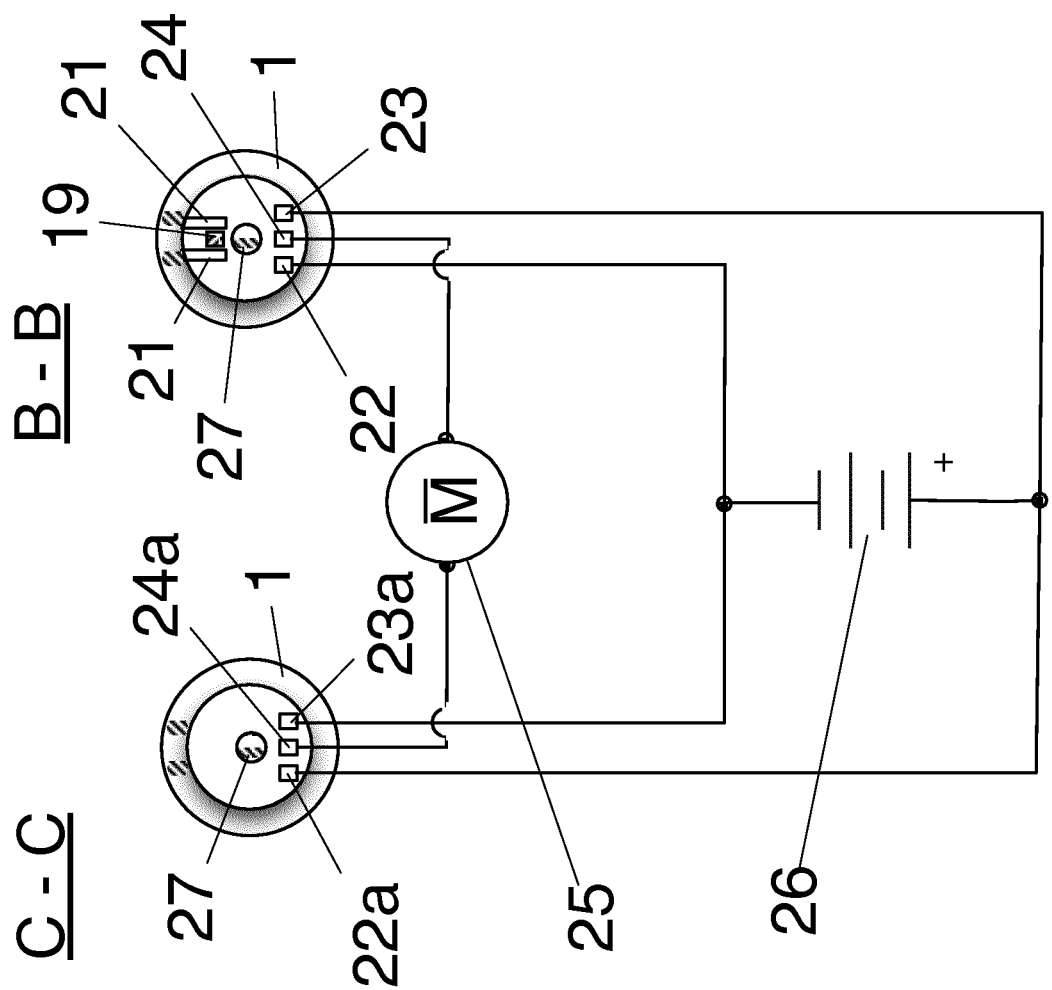
FIG. 5 is a cross-section along the line B-B of FIG. 2 and a cross-section along the line C-C of FIG. 2 with an example of the wiring diagram of the toothbrush.

In the second embodiment of the invention, shown in FIGS. 2, 3, and 5, the head of the toothbrush is empty inside 15 and is equipped with a pair of cylindrical brushes 16, said brushes constituting the working element of the toothbrush. The brushes 16 are able to rotate in both directions, to the right or to the left, in such a manner that they always rotate in opposite directions. In this example, the head 15 of the toothbrush has an elongated neck 17, said head being thus distanced from the handle 1.

The head 15 is rotatably mounted in the handle 1 through a cylindrical base 18, said base extending inside the handle 1 generally close to its end.

The cylindrical base 18 of the head 15 has a resilient technical means and a rotating coupling means in the form of two protrusions 19 and 20, which are being placed axially and opposite to each other. The resilient technical means or the first protrusion 19 being resilient and the rotating technical means or the second protrusion 20 being stiff. The body of the handle 1 has two inner short ribs 21 placed internally and inside, close to an end of said handle 1 on the neck part side 17 of the head 15. The two inner short ribs 21 are located adjacent to both sides of the first protrusion 19 such that the first protrusion 19 is placed between these two inner short ribs 21 of the handle 1. Moreover, the body of the handle 1 has two pairs of electric contacts, 22, 23 and 22*a*, 23*a*, disposed opposite to said inner short ribs 21 and being stationary with respect to said handle 1. The pairs of electric contacts 22, 23 and 22*a*, 23*a*, are placed at a distance on both sides of the second protrusion 20 of the base 18 of the head 15. The second protrusion 20 is equipped with the third pair of electric contacts 24 and 24*a*, which are movable with respect to the handle 1.

Consequently, the base 18 of the head 15 can be rotated with respect to the handle by a small acute angle in both directions, i.e., to the right or to the left from the standby (equilibrium) position, in which it is kept by the resilient protrusion 19, said protrusion being mounted between the ribs 21 of the handle 1. It is clear for an expert that such movement is possible within the limits of the elasticity of the first protrusion 19 and that such movement is limited by the distance between stationary pairs of contacts 22, 23 and 22*a*, 23*a* of the handle 1 and the third pair of contacts, 24 and 24*a*, placed at the second protrusion 20 of the base 18 of the head 15.

The brushes 16 are driven by an electric motor 25, which is mounted in the cylindrical handle 1 of the toothbrush together with the power source 26 in the form of galvanic cells or accumulators.

The end of the drive shaft of the motor 25 is shape coupled 27 to the transmission shaft 28, said transmission shaft being located inside the neck 17 of the head 15, coaxially to the rotation axis of the base 18 of the head 15 with respect to the handle 1.

In the empty socket of the head 15, the transmission shaft 28 is coupled to the fixtures 30 of two rotating brushes 16 by means of two angular gears 29. Both fixtures 30 are placed next to each other at such an angle that their rotation axes intersect beyond the outline of the handle 1, and the fixtures 30 are placed eccentrically with respect to the rotation axis of the base 18 of the head 15 with respect to the handle 1 of the toothbrush.

As a result of the eccentric placement of said elements, when using a toothbrush the user presses the bristles of the brushes 16 against the teeth 10, the pressure force of the teeth 10 on the brush 16 causes the rotation of the base 18 of the head 15 with respect to the handle 1, from the equilibrium position, in which it is kept by the resilient protrusion 19. The movement to the right or to the left depends on the orientation and direction of the pressure force of the teeth 10 on the brush 16.

Similarly, as described in the first example, the rotational movement of the head 15 with respect to the handle 1 is used to start and stop the motor 25 and to change the motor 25 rotation direction to the right or to the left, whereby the brushes 16 will always make the rotating movement "sweeping" the deposits in the direction from the gums 11 to the biting edge of the teeth 10. It is thus understandable that for this purpose, two pairs of stable electric contacts, 22, 23 and 22*a*, 23*a*, of the handle 1, and one pair of movable contacts, 24 and 24*a*, placed at the second protrusion 20 of the base 18 of the head 15, are connected accordingly to the wires of the electric circuit to control the motor 25 and the power source 26.

Similar to the first example, electric wiring of the toothbrush was omitted in FIG. 2 for better readability. However, it is shown by way of example in FIG. 5.

Figure 8:
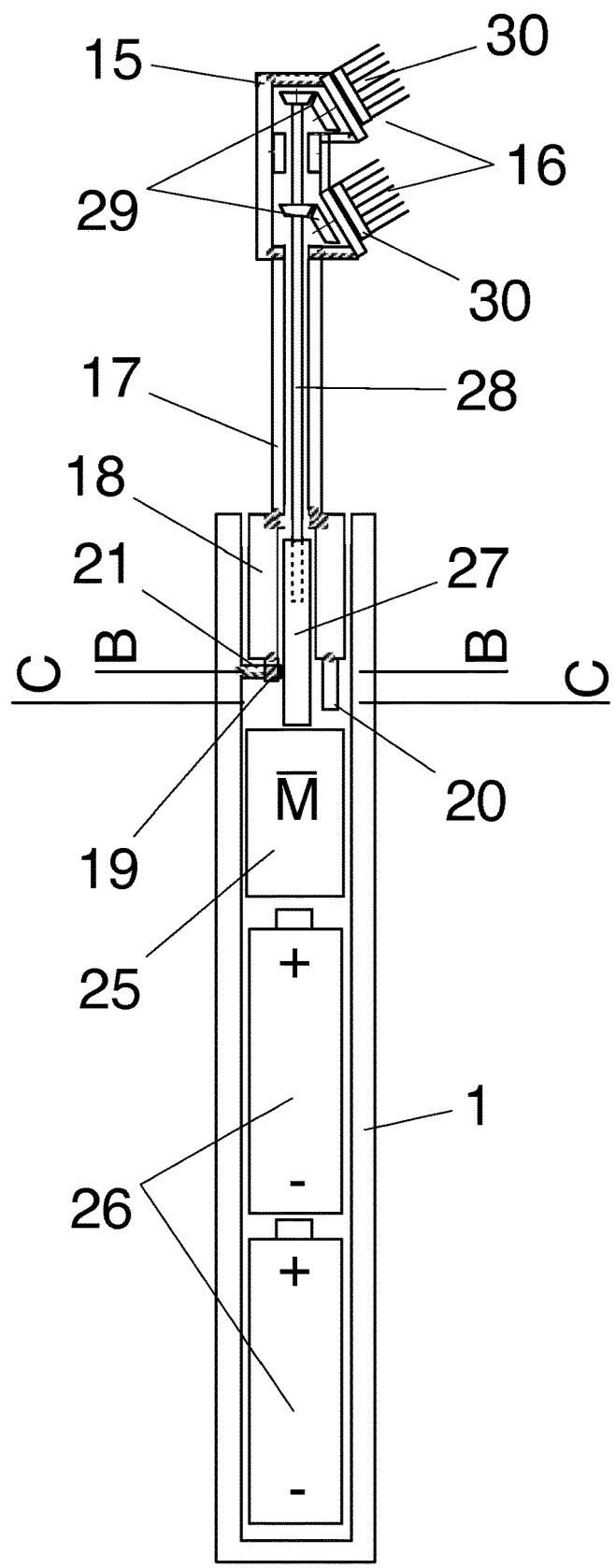
FIG. 8 illustrates a longitudinal section of the toothbrush in the third embodiment.

In the third embodiment of the invention, shown in FIG. 8, the head 15 of the toothbrush is empty inside and is equipped with a pair of cylindrical brushes In 16, said brushes constituting the working element of the toothbrush. In the empty socket of the head 15, the transmission shaft 28 is coupled to the fixtures 30 of two rotating brushes 16 by means of two angular gears 29, similarly as described in the second example. this example, both fixtures 30 are placed next to each other such that their rotation axes are parallel or they intersect at an obtuse angle and—in such case—the rotation axes do not intersect beyond the outline of the handle 1, and the fixtures 30 are placed eccentrically with respect to the rotation axis of the base 18 of the head 15 with respect to the handle 1 of the toothbrush.

As a result of the parallel or obtuse placement of said elements, the bristles of the most outer brush 16 stick beyond the outline of the head 15, causing better operation range of the brushes 16 in the mouth especially when using a toothbrush for brushing most inner teeth. Parallel arrangement is preferred in this embodiment. Although FIG. 8 presents both working elements 16 oriented "upwards", i.e. in the direction away from the handle 1, the working elements 16 may alternatively be oriented "downwards", i.e. in the direction towards the handle 1.

Figure 6:
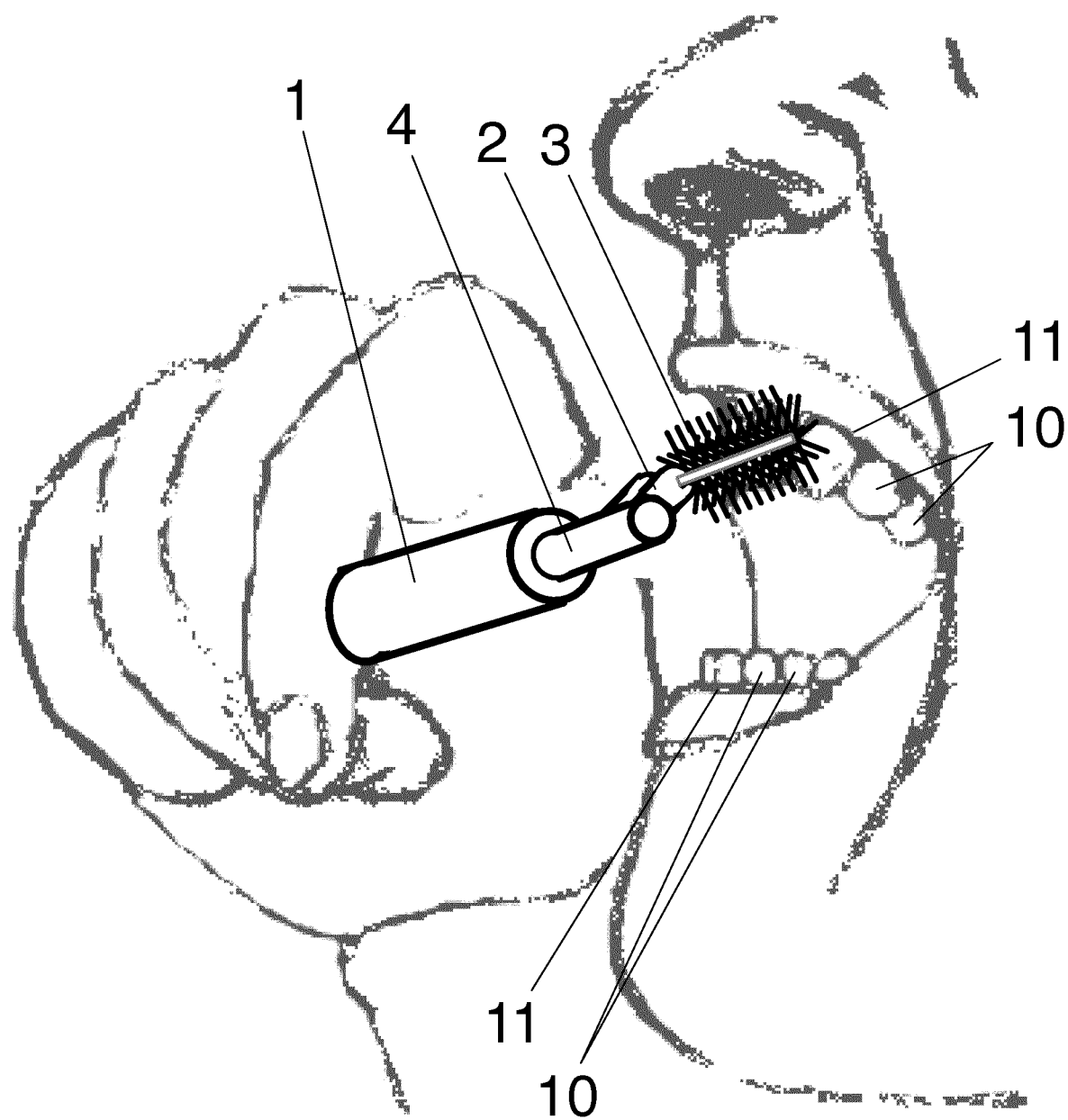
FIG. 6 illustrates one use of the toothbrush according to another embodiment.
Figure 7:
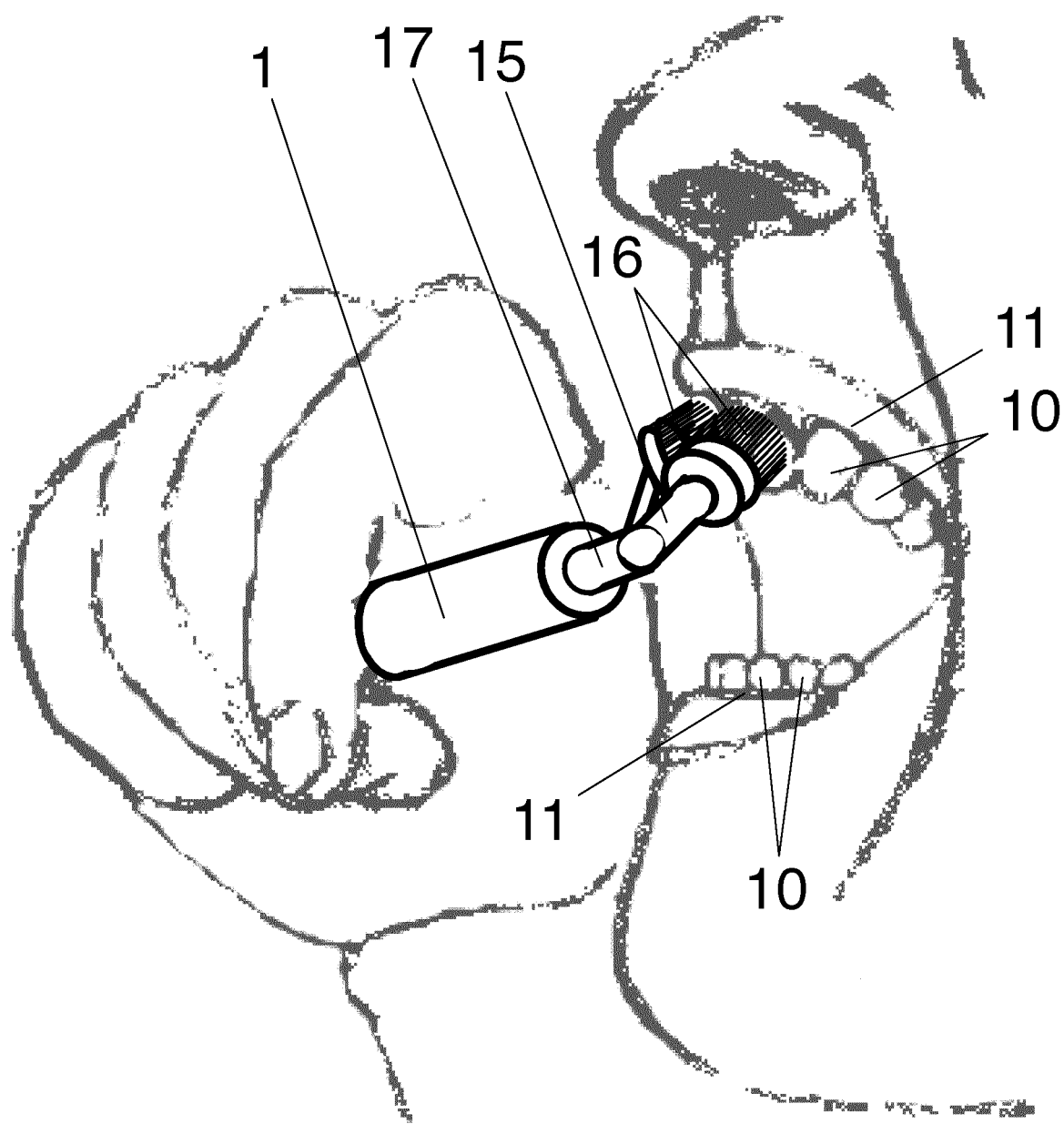
FIG. 7 illustrates another use of the toothbrush according to yet another embodiment.

The principle of the control of the rotation direction during the operation of the toothbrush is presented in FIGS. 6 and 7, showing subsequent examples of the execution of the invention, which are similar to the first, second and third embodiments presented above in detail.

Turning on the toothbrush is best achieved by pressing the brushes 3, 16 against the teeth 10 and making the rotation of the handle 1 with a "sweeping" movement in the direction from the gum 11 to the biting edge of the teeth 10, and against the elasticity forces of the resilient element coupling the handle 1 with the base 4, 18 of the head 2, 15 and keeping said handle 1 and base 4, 18 in the standby (equilibrium) position in which the toothbrush is turned off. Releasing the pressure exerted by the brushes 3, 16 on the teeth 10 causes the rotation of the handle 1 to the equilibrium position in which the motor of the toothbrush is turned off.

The movement turning on the inventive toothbrush is therefore identical to a typical "sweeping" movement made when brushing the teeth with a manual (traditional) toothbrush, because the rotation axes of the base 4 with respect to the handle 1 and the rotation axes of the brushes 3, 16 are similarly spatially oriented. This makes it essentially easier to use the device while maintaining the brushing skills acquired by the use of traditional toothbrushes.

A relative position and shape of the handle 1, the head 2, 15, and the brushes 3, 16 makes it practically impossible to use the device when the brushes 3, 16 are placed in the mouth in such manner that the handle 1 and the head 2, 15 are directed towards the gums 11, and the brushes 3, 16 are directed towards the teeth 10. Consequently, it is impossible to turn on the toothbrush in such a manner that the rotating movement of the bristles of the brushes 3, 16 in the direction from the teeth 10 towards the gum 11 is produced, because then it would be necessary to push the brushes 3, 16 against inner cheeks or against the lips or against the tongue instead of the teeth.

Turning on the toothbrush is accomplished by making a "sweeping", rotating movement with the handle 1 in the direction from the gum 11 to the teeth 10 with a simultaneous placement of the brush 3, 16 against the brushed surface in order to overcome the elasticity forces from the resilient element, coupling the handle 1 and the base 4, 18 and deformed by this movement. Consequently, the brush 3, 16 of the powered toothbrush is rotating in such a direction that the bristles are moving from the gum 11 towards the biting edge of the teeth 10.

The construction of the toothbrush according to the invention, in which in order to power the device it is necessary to rotate the base 4, 18 of the head 2, 15 with respect to the handle 1, makes it impossible to place the device in the mouth and turn it on in an incorrect position, because of insufficient space between the gum and inner cheeks or tongue, wherein a part of the head 2, 15 would need to be placed, and, moreover, because of the lack of pressure force that the teeth 10 exert on the brush 3, 16, said force being necessary to turn the handle 1 and power the motor driving the brushes 3, 16.

The invention claimed is:

1. An electric toothbrush comprising:
   a handle;
   a head movable with respect to said handle, wherein the head is provided with a rotating working element having at least one brush which is located out of the geometric axis of said handle;
   an electric motor for driving the rotating working element in a rotary movement in a clockwise or counterclockwise direction; and
   a motor rotation direction switch coupled functionally with said head and said handle, wherein:
   the head is joined with the handle by a rotating coupling means,
   the rotating working element is mounted on the head so as to be located out of the rotation axis of the head with respect to the handle and is configured to generate a torque solely through pressing said rotating working element on the tooth,
   the head and the handle are coupled with a resilient technical means, said resilient technical means enable, after exertion of the torque to the head, to rotate the head with respect to the handle into the left or right positions, where the motor rotation direction switch turns on the motor in the clockwise or counterclockwise rotation direction, and after release of the torque, the resilient technical means enable to maintain the head in a standby position relative to the handle where the motor rotation direction switch coupled with the head and the handle turns off the motor, wherein the pressure of the brush on the tooth produces the torque that causes a rotational movement of the head with respect to the handle, due to the eccentric placement of the working element with respect to the axis of the rotation of the head in the handle,
   wherein the rotating coupling means comprises a longitudinal slit placed axially at one end of a base of the head with edges situated at a distance from both sides of the resilient technical means, said resilient technical means comprises a rib being located radially in the handle and being shape-coupled with its end to the base of the head, and
   wherein said rib is provided with a first electric contact of the motor rotation direction switch, and the edges of said slit are provided with a second and a third electric contact of the motor rotation direction switch, each situated at a distance on both sides of the first electric contact.

2. The electric toothbrush according to claim 1, wherein the head is pivotally mounted on the handle through a base which extends inside of the handle is coupled with a resilient rib of said handle.

3. The electric toothbrush according to claim 2, wherein a cylindrical brush is mounted on the head with a rotation axis, which is shifted eccentrically with respect to the rotation axis of the base of the head with respect to the handle.

4. The electric toothbrush according to claim 1, wherein the head is pivotally mounted on the handle through a base, said base is provided with a first resilient protrusion coupled with a pair of inner short ribs from within the handle.

5. The electric toothbrush according to claim 4, wherein the base of the head has a second protrusion, placed opposite to the first resilient protrusion, said first resilient protrusion being fixed between the pair of inner short ribs of the handle.

6. The electric toothbrush according to claim 5, wherein the second protrusion of said base of the head is equipped with one electric contact of the motor rotation direction switch, and two other electric contacts of the motor rotation direction switch are fixed within the handle, and said two other electric contacts are located at a distance on both sides of the first electric contact.

7. The electric toothbrush according to claim 5, wherein the second protrusion of said base of the head is provided with a pair of first electric contacts of the motor rotation direction switch, and two pairs of second electric contacts of the motor rotation direction switch are fixed within the handle, located at a distance on both sides of said pair of first electric contacts.

8. The electric toothbrush according to claim 1, wherein a pair of cylindrical brushes is fitted in the head, said brushes having fixtures located eccentrically with respect to the rotation axis of the base of the head with respect to the handle.

9. The electric toothbrush according to claim 8, wherein the fixtures of said pair of cylindrical brushes are placed next to each other at such an angle that their rotation axes intersect outside the contour of the handle.

10. The electric toothbrush according to claim 8, wherein the fixtures of said pair of cylindrical brushes are placed next to each other at such an angle that their rotation axes do not intersect outside the contour of the handle, so that their rotation axes are parallel to each other.

* * * * *